(12) United States Patent
Williams

(10) Patent No.: US 8,595,165 B2
(45) Date of Patent: Nov. 26, 2013

(54) METHOD FOR DIAGNOSING URTICARIA AND ANGIOEDEMA

(75) Inventor: Paul Eirian Williams, Cardiff (GB)

(73) Assignee: Time for Medicine Limited, Cardiff (GB)

(*) Notice: Subject to any disclaimer, the term of this patent is extended or adjusted under 35 U.S.C. 154(b) by 151 days.

(21) Appl. No.: 13/144,545

(22) PCT Filed: Jan. 14, 2010

(86) PCT No.: PCT/GB2010/050052
§ 371 (c)(1),
(2), (4) Date: Nov. 4, 2011

(87) PCT Pub. No.: WO2010/082057
PCT Pub. Date: Jul. 22, 2010

(65) Prior Publication Data
US 2012/0041915 A1    Feb. 16, 2012

(30) Foreign Application Priority Data
Jan. 15, 2009   (GB) .................................. 0900622.2

(51) Int. Cl.
*G06N 5/00*   (2006.01)

(52) U.S. Cl.
USPC ............................................. 706/20; 706/45

(58) Field of Classification Search
USPC .................................................. 706/20, 45
See application file for complete search history.

(56) References Cited

U.S. PATENT DOCUMENTS
2011/0276344 A1 * 11/2011 Williams ............................ 705/2

FOREIGN PATENT DOCUMENTS
WO       9905487 A1    2/1999
WO    2009007734 A1    1/2009

OTHER PUBLICATIONS

Barnert, et al., Diagnosis and Management of Lower Gastrointestinal Bleeding, Nature Reviews, Gastroenterology & Hepatology, vol. 6, Nov. 2009, pp. 637-646.*
Chae YM et al "The Development of a Decision Support System for Diagnosing Nasal Allergy", Yonsei Medical Journal, Yonsei University, vol. 33, No. 1, 1992, pp. 72-80.
Young Moon & Chae et al "Comparison or Alternative Knowledge Models for the Diagnosis of Asthma" Expert Systems with Applications, vol. 11, No. 4, 1996, pp. 423-429.
Park KS et al "Developing a Knowledge-Based System to Automate the Diagnosis of Allergic Rhinitis", Biomedical Fuzzy and Human Sciences: The Official Journal of the Biomedical Fuzzy Systems Association, vol. 2, No. 1, 1996, pp. 9-18.

* cited by examiner

*Primary Examiner* — Wilbert L Starks
(74) *Attorney, Agent, or Firm* — King & Schickli, PLLC

(57) ABSTRACT

According to the invention there is provided a method for diagnosing urticaria or angioedema including: (a) asking a patient the following questions: are any NSAIDs or aspiring being taken; are symptoms triggered by aspirin, aspirin-containing drugs, orange juice, curry or high-aspirin content food; is tingling of the mouth or lips, swelling of the tongue, the inside of the mouth or throat, difficulty swallowing, or difficulty breathing experienced after other medications than those known to cause urticaria or angioedema; does urticaria or angioedema come on with physical stimuli such as cold, wet, wind and pressure; (b) carrying out one or more tests which includes a RAST test to cat; (c) inputting the results of the questions and tests into a neural network that has been trained to diagnose urticaria or angioedema; and (d) producing an output indicative of urticaria or angioedema.

17 Claims, 3 Drawing Sheets

FIGURE 1: Role of CardiffTELE*form* Information Capture System v8.2

METHOD FOR DIAGNOSING URTICARIA AND ANGIOEDEMA

This application is the national stage of PCT/GB2010/050052, filed Jan. 14, 2010, which claims priority from British Patent Application Ser. No. 0900622.2, filed Jan. 15, 2009, the disclosures of which are incorporated herein by reference.

FIELD OF THE INVENTION

This invention relates to a method and means, including parts thereof, for diagnosing urticaria and angioedema using an artificial neural network (ANN). The invention involves obtaining information about a patient, based on asking the patient a series of selected questions and carrying out a number of selected tests, inputting this information into a neural network, and obtaining a preliminary diagnosis. The invention applies equally to adults and children.

BACKGROUND OF THE INVENTION

Allergies currently affect approximately 34% of the general population (Linneberg 2000). Whilst at one extreme serious conditions such as anaphylaxis can be life threatening, most allergic disorders pose little risk of death. However, diseases such as urticaria and angioedema cause distress and misery for millions of patents, often at times in their lives when they should be most active (Holgate and Broide 2003). Urticaria (or hives) is a skin rash which occurs in the upper dermis. Angioedema (also known as Quincke's edema) is a swelling of the dermis, subcutaneous tissue, mucosa and submucosal tissues. Allergic diseases are a significant cause of morbidity in modern society, adversely affecting sleep, intellectual functioning and recreational activities. Furthermore, allergic diseases exert a profoundly negative impact on occupational performance and have major public health costs.

Across the United Kingdom, waiting times for specialist allergy consultations following referral from primary care are long.

The rising prevalence of allergies and the associated demand for specialist services suggest that waiting times will inevitably lengthen over the course of the next decade. Given that there is currently an acute shortage of Immunologists and Allergists in the UK and worldwide, it seems unlikely that sufficient medical manpower will emerge in the foreseeable future to deal with this increasing demand.

Recent in-house research has centred on the role of the Allergy Nurse Practitioner in the diagnosis and management of allergic disease. Increasing use of the Nurse Practitioner in a diagnostic role would enable waiting times to be shortened and new patient referrals to be seen without the presence of the Consultant Clinical Immunologist. Whilst Nurse Practitioner-based diagnosis and management strategies should, in time, ameliorate the critical situation, a parallel increase in demand for allergy services will, without doubt, limit the positive effects on waiting times. There therefore remains a need to develop further innovative methods to facilitate access of patients to clinical diagnostic services.

However, as one would expect, it is extremely important that any new methods of diagnosis are accurate if they are to be adopted by the medical community at large. These methods must be able to replicate, if not exceed, the accuracy of an experienced Clinical Immunologist. This is a difficult task to achieve because a Clinical Immunologist uses information from a vast number of sources when reaching a diagnosis.

Typically, when diagnosing a condition, a medical practitioner will integrate information from several sources, such as a medical history, a physical examination, the results of clinical tests, and by asking the patient about his/her condition. The medical practitioner will use judgement based on experience and intuition, both when deciding what to look for and in analysing the information, in order to come to a particular diagnosis.

Thus, the process of diagnosis involves a combination of knowledge, intuition and experience that leads a medical practitioner to ask certain questions and carry out particular clinical tests, and the validity of the diagnosis is very dependent upon these factors.

Given the predictive and intuitive nature of medical diagnosis, and the fact that specialist, experienced medical practitioners are in demand, we have attempted to replicate the diagnostic process in an automated system, in order to give a wider audience access to this service. We have found that artificial neural networks (ANNs) have characteristics that make them particularly well suited for this purpose.

ANNs are computational mathematical modelling tools for information processing and may be defined as 'structures comprised of densely interconnected adaptive processing elements (nodes) that are capable of performing massively parallel computations for data processing and knowledge representation' (Hecht-Nielsen 1990; Schalkoff 1977). Single artificial neurons for the computation of arithmetic and logical functions were first described by McCulloh and Pitts (1943); fifteen years later Rosenblatt (1958) described the first successful neurocomputer (the Mark 1 Perceptron). This simple network consisted of two layers of neurons connected by a single layer of weighted links and was capable of solving problems in a way analogous to information processing in the human brain (Wei et al 1998; Basheer and Hajmeer 2000). These early structures were however unable to predict generalised solutions for complex non-linear problems. Over the course of the following five decades complexity has increased with the development of multiple networked perceptrons; such advances have led to the application of ANNs to a colossal number of problems, and by 1994 more than 50 different types of network were in existence (Pham 1994 and Basheer and Hajmeer 2000), each possessing unique properties enabling them to solve particular tasks.

Such ANNs are capable of dealing with non-linear data, fault and failure, high parallelism and imprecise and fuzzy information (Wei et al 1998). Neural networks have been shown to be capable of modelling complex real-world problems and found extensive acceptance in many scientific disciplines (Callan 1999). The decision as to which type of ANN should be utilised for a particular task depends on problem logistics, input type, and the execution speed of the trained network (Basheer and Hajmeer 2000).

Neural networks have found increasing application in a range of clinical settings where they have produced accurate and generalised solutions compared to traditional statistical methodology (reviewed Baxt 1995, Wei et al 1998, Dybowski and Gant 2001). For example, U.S. Pat. No. 6,678,669 discloses using an ANN to diagnose endometriosis, predicting pregnancy related events, such as the likelihood of delivery within a particular time period, and other such disorders relevant to women's health.

The most commonly used ANN in such studies is the Backpropagational Multilayer Perceptron (MLP). MLPs are particularly useful in solving pattern classification problems (Wei et al 1998; Basheer and Hajmeer, 2000), which are common in the clinical arena. In this context the ANN looks for patterns in a similar way to learning in the human mind;

the more a particular pattern is represented, the stronger the recognition of it by the network.

We have developed a method of diagnosing urticaria and angioedema using a neural network. In particular, from the vast amount of information that a clinician would have available, we have identified a manageable set of questions and tests that have clinical significance, and can be used to train a neural network to diagnose urticaria and angioedema, and by inputting the results of these questions and tests into a neural network thus trained the network to produce a diagnosis.

Surprisingly, we have found that a small set of just 5 inputs to the neural network have a profound influence on the provision of an accurate diagnosis. The 5 inputs are generated by asking a patient 4 questions and carrying out 1 medical test, and are referred to herein as the 5-input model.

We have also identified a set of 14 (13 questions and 1 test), 15 (13 questions and 2 tests) 17 (14 questions and 3 tests), 21 (16 questions and 5 tests), 25 (20 questions and 5 tests), 35 (23 questions and 12 tests), 54 (36 questions and 17 tests), and 79 (42 questions and 36 tests) inputs, referred to herein as the 14, 15, 17, 21, 25, 35, 54 and 79 input models respectively, that can be input into a neural network to obtain a diagnosis.

The identification of these clinically significant questions and tests will mean that a neural network can be trained to diagnose urticaria or angioedema in considerably less time than it currently takes a consultant, which in turn will save time and money.

Additionally, a neural network offers an easy-to-use means of diagnosis, both for clinicians and non-clinicians, and will allow central aspects of diagnosis and management to be performed electronically in a way that is accessible to systematic audit and reduce inequalities in accessing allergy services, via the use of remote electronic information transfer.

For the avoidance of doubt, any reference herein to a neural network is a reference to an artificial neural network (ANN).

SUMMARY OF THE INVENTION

According to a broad aspect of the invention, there is provided a method for diagnosing urticaria or angioedema including: asking a patient a set of questions and/or carrying out one or more tests; inputting the results of the questions and tests into a neural network that has been trained to diagnose urticaria or angioedema; and producing an output indicative of urticaria or angioedema.

According to a first aspect of the invention, there is therefore provided a method for diagnosing urticaria or angioedema including:
(a) asking a patient a set of questions which includes the following questions:
 are any NSAIDs (non-steroidal anti-inflammatory drugs) or aspirin being taken;
 are symptoms triggered by aspirin, aspirin-containing drugs, orange juice, curry or high-aspirin content food;
 is tingling of the mouth or lips, swelling of the tongue, the inside of the mouth or throat, difficulty swallowing, or difficulty breathing experienced after other medications than those known to cause urticaria or angioedema;
 does urticaria or angioedema come on with physical stimuli such as cold, wet, wind and pressure;
(b) carrying out one or more tests which includes a RAST test to cat;
(c) inputting the results of the questions and tests into a neural network that has been trained to diagnose urticaria or angioedema; and
(d) producing an output indicative of urticaria or angioedema.
This is referred to as the 5-input model.

In a preferred method of the invention, part (a) further includes asking the patient the following questions:
 are any drugs that are associated with urticaria or angioedema, other than ACE (Angiotensin Converting Enzyme) inhibitors, A2R (Angiotensin-2 receptor) antagonists, statins, PPI (Proton Pump Inhibitors), SSRI (Selective Serotonin Reuptake Inhibitors), SNRI (Serotonin and Noradrenaline Reuptake Inhibitors), NSAIDs, aspirin, OCPill (Oral Contraception Pill), HRT (Hormone Replacement Therapy) or bisphosphonates, being taken;
 optionally, are any other drugs which can cause the symptoms complained of being taken or have recently been taken;
 is tingling of the mouth or lips, swelling of the tongue, the inside of the mouth or throat, difficulty swallowing, or difficulty breathing experienced after foods;
 is wheezing or a worsening of asthma or eczema experienced after eating foods;
 are symptoms triggered by fruit and vegetables;
 are symptoms triggered by unidentified food additives;
 the time elapsed between eating a food implicated with causing symptoms and the symptoms appearing;
 how frequently the symptoms occur; and
 what areas of the body are affected by a rash.
This is referred to as a 14-input model.

Examples of drugs that are associated with urticaria or angioedema include opiates, nicorandil, amlodipine, X-ray contrast media and chlorthalidone. Other examples are known to the skilled person.

In a further preferred method of the invention, part (b) further includes carrying out a skin prick test (SPT) to cat.
This is referred to as a 15-input model.

In yet a further preferred method of the invention:
 part (a) further includes asking the patient the following question:
  do new rash patches appear when old rash patches are disappearing;
 and part (b) further includes carrying out a skin prick test to a plurality of nuts to determine if there is a reactivity to any one of them.
This is referred to as a 17-input model.

Typically, the test under part (b) includes carrying out a skin prick test to peanut, hazelnut, almond, walnut and brazil nut. Other selections of nuts may suggest themselves to the skilled person.

In yet a further preferred method of the invention:
 part (a) further includes asking the patient the following questions:
  is swelling of the lips, eyelids or tongue experienced;
  is an itchy, red, raised, burning and hot nettle rash experienced;
 and part (b) further includes carrying out the following tests:
  RAST test to HDM (house dust mite);
  RAST test to a plurality of nuts in order to determine the highest quantitative result;
 and part (c) includes inputting the highest quantitative result from the RAST test to the plurality of nuts.
This is referred to as a 21-input model.

In yet a further preferred method of the invention:
 part (a) further includes asking the patient the following questions:
  number of first degree relatives with asthma, rhinitis or eczema;
  are symptoms triggered by wheat;

are symptoms triggered by foods other than wheat, egg, milk, cheese, peanut, other nuts, fish or shellfish;
length of time that rash or swelling has been experienced.

This is referred to as a 25-input model.

In yet a further preferred method of the invention:
part (a) further includes asking the patient the following questions:
is a nettle rash experienced after foods;
are symptoms triggered by cheese;
if antihistamines have been taken for urticaria, were they effective;
and part (b) further includes carrying out the following tests:
skin prick test to HDM;
skin prick test to grass pollens;
skin prick test to egg;
skin prick test to milk;
total serum (IgE) detected;
RAST test to tree pollens;

This is referred to as a 35-input model.

In yet a further preferred method of the invention:
part (a) further includes asking the patient the following questions:
is an ACE inhibitor being taken;
is an A2R antagonist being taken;
is a statin being taken;
is PPI being taken;
is SSRI being taken;
is SNRI being taken;
is OCPill being taken;
is HRT being taken;
is a bisphosphonate being taken;
number of pack years smoked;
is nausea, vomiting, abdominal pain or diarrhoea experienced after foods;
are headaches experienced after foods;
how long do rash patches last for;
and part (b) further includes carrying out the following tests:
RAST test to grass pollens;
RAST test to egg;
RAST test to wheat;
RAST test to apple;
one or more RAST tests to any fruit, vegetable or other food (other than egg, milk, soya, wheat, fish, rice, peanut, hazelnut, brazil nut, almond, walnut or apple) associated with symptoms;
and part (c) includes inputting which fruit, vegetables are associated with the symptoms and the results of the associated RAST tests.

This is referred to as a 54-input model.

The question 'how long do rash patches last for' may be coded for a yes/no answer. For example, whether the patches last for longer or shorter than a defined period of time, such as 24 hours.

In yet a further preferred method of the invention:
part (a) further includes asking the patient the following questions:
are symptoms triggered by egg;
are symptoms triggered by milk;
are symptoms triggered by peanut;
are symptoms triggered by other nuts;
are symptoms triggered by fish;
are symptoms triggered by shellfish;
and part (b) further includes carrying out the following tests:
skin prick tests for dog, tree pollens, rice, peanut; hazelnut, brazil nut, almond, walnut, and latex;
RAST tests for dog, soya, fish, rice, peanut, hazelnut, brazil nut, almond, walnut and latex.

This is referred to as a 79-input model.

Generally, the results of the tests under part (b) are provided as quantitative results. The quantitative results may relate to the amount of allergen-specific IgE antibodies present. The results of the tests under part (b) above may be provided with a graded result and so represent an incremental unit indicative of the nature of the response. Alternatively, the results may represent a measure of a unit from a continuous scale, such as kilo units of allergen-specific IgE antibodies per litre.

Grass and tree pollens referred to herein may be selected having regard to the geographical region in which the patient lives. For example, in the UK, one would test for mixed grass pollens whereas in North America one is much more likely to include ragweed and in Northern Europe a test for tree pollen is likely to includes a test for tree birch. As will be apparent to the man skilled in the art the geographically representative allergens are well known in each geographical region and would be selected on the basis that in each region the selected allergens are known to elicit an allergic reaction of the upper respiratory tract.

The RAST test is undertaken using an antibody that is labelled with a suitable label such as a radio-label, although light emitting labels may be used as an alternative, and conventional techniques are used in order to measure the patient's immune status. RAST tests, and variations thereof, are well known to those skilled in the art and indeed have been performed for many decades. The original disclosure concerning diagnosis of an allergy by an in vitro test for allergen antibodies was described by Wide et al in 1967 and has further been assessed by Thomson & Bird, 1983.

In some cases it may be useful to save results for analysis at a later time, for example if they cannot be obtained simultaneously. In this instance the results may be stored on a computer system and applied to a neural network subsequently.

In another aspect of the invention, there is provided a computer system or apparatus, configured to aid in the diagnosis of urticaria or angioedema, including:
(a) a device for obtaining data relating to a patient, wherein the data includes the results of a combination of questions and tests outlined in the first aspect of the invention;
(b) optionally, a device for storing the data in storage means of the computer system;
(c) a device for transferring the data to a neural network trained on samples of the data; and
(d) a device for extracting from the trained neural network an output, the output being an indicator for the diagnosis of urticaria or angioedema.

For the avoidance of doubt, in the computer system or apparatus the data may include information obtained using the 5-, 14-, 15-, 17-, 21-, 25, 35-, 54- or 79-input models, or any selected combination thereof.

As will be appreciated, this aspect of the invention may also be adapted so that the computer is linked to an intranet or Internet with a neural network, thereby allowing patients and/or medical practitioners to input information from remote locations and obtain a preliminary diagnosis.

According to a further aspect of the invention there is provided a neural network to aid in the diagnosis of urticaria or angioedema, the neural network including:

an input layer having a plurality of input nodes into which can be inputted data which include the results of a combination of questions and tests outlined in the first aspect of the invention; and an output layer for producing an output;

in which the neural network is trained on data relating to a group of patients in which urticaria or angioedema is present, wherein the data include said results of said combination of questions and tests according to the first aspect of the invention; so that the neural network is configured to identity a pattern of data which corresponds to urticaria or angioedema by the output layer producing an output indicative of the diagnosis of urticaria or angioedema.

The neural network may be present on a computer or computer system. The neural network may be present on a server so that it can be accessed remotely.

The results of any of the 5-, 14-, 15-, 17-, 21-, 25-, 35-, 54- and 79-input models, or any selected combination thereof, may also be used to train a neural network to diagnose a condition.

Accordingly, in a yet further aspect of the invention there is provided a method for training a neural network to aid in diagnosing urticaria or angioedema, including:

a) obtaining data relating to a group of patients in which urticaria or angioedema is known, wherein the data include a combination of the results of the questions and tests outlined in the first aspect of the invention;

(b) training a neural network to identify a pattern of data which corresponds to urticaria or angioedema; and (c) storing the neural network in storage means of a computer or on a computer-readable medium.

A neural network may also be trained using other methods, which methods will be apparent to a man skilled in the art.

The invention further comprises a computer or a computer system comprising at least one neural network embodying any one or more of the aforementioned models or methods for the purposes of performing a diagnosis.

The invention further comprises at least one neural network that has been trained for diagnosis using data from the 5-, 14-, 15-, 17-, 21-, 25-, 35-, 54- or 79-input models. Such a neural network may be sold separately, or put on a server so that it can be accessed remotely.

Yet further, the invention comprises a data carrier comprising the aforementioned methodology of the invention and/or a software interface for enabling a user to communicate with a neural network trained for the diagnostic purpose of the invention.

According to another aspect of the present invention there is provided a computer program product including:

a computer usable medium having computer readable program code and computer readable system code embodied on said medium for aiding in the diagnosis of urticaria or angioedema, said computer program product including:

computer program code means, when the program code is loaded, to make the computer execute a procedure to:

(a) obtain data relating to a patient, wherein the data include the results of a combination of questions and tests outlined in the first aspect of the invention;

(b) optionally, store the data;

(c) transfer the data to a neural network trained on the aforementioned data; and (d) extract from the trained neural network an output, the output being an indicator for the diagnosis of urticaria or angioedema.

According to a further aspect of the invention there is provided a computer system including a first means for:

(a) obtaining data relating to a patient, wherein the data include the results of a combination of questions and tests outlined in any the first aspect of the invention; and a second remote means, wherein said second means includes means for:

(b) optionally, storing the data;

(c) transferring the data to a neural network trained on the aforementioned data; and (d) extracting from the trained neural network on output, the output being an indicator for the diagnosis of urticaria or angioedema.

Whilst the invention has been described above, it extends to any inventive combination of the features set out above, or in the following description, drawings or claims.

BRIEF DESCRIPTION OF THE DRAWING FIGURES

Methods and results in accordance with the present invention will now be described with reference to the following drawings, in which:—

DETAILED DESCRIPTION OF THE INVENTION

Example 1

Figure 1:
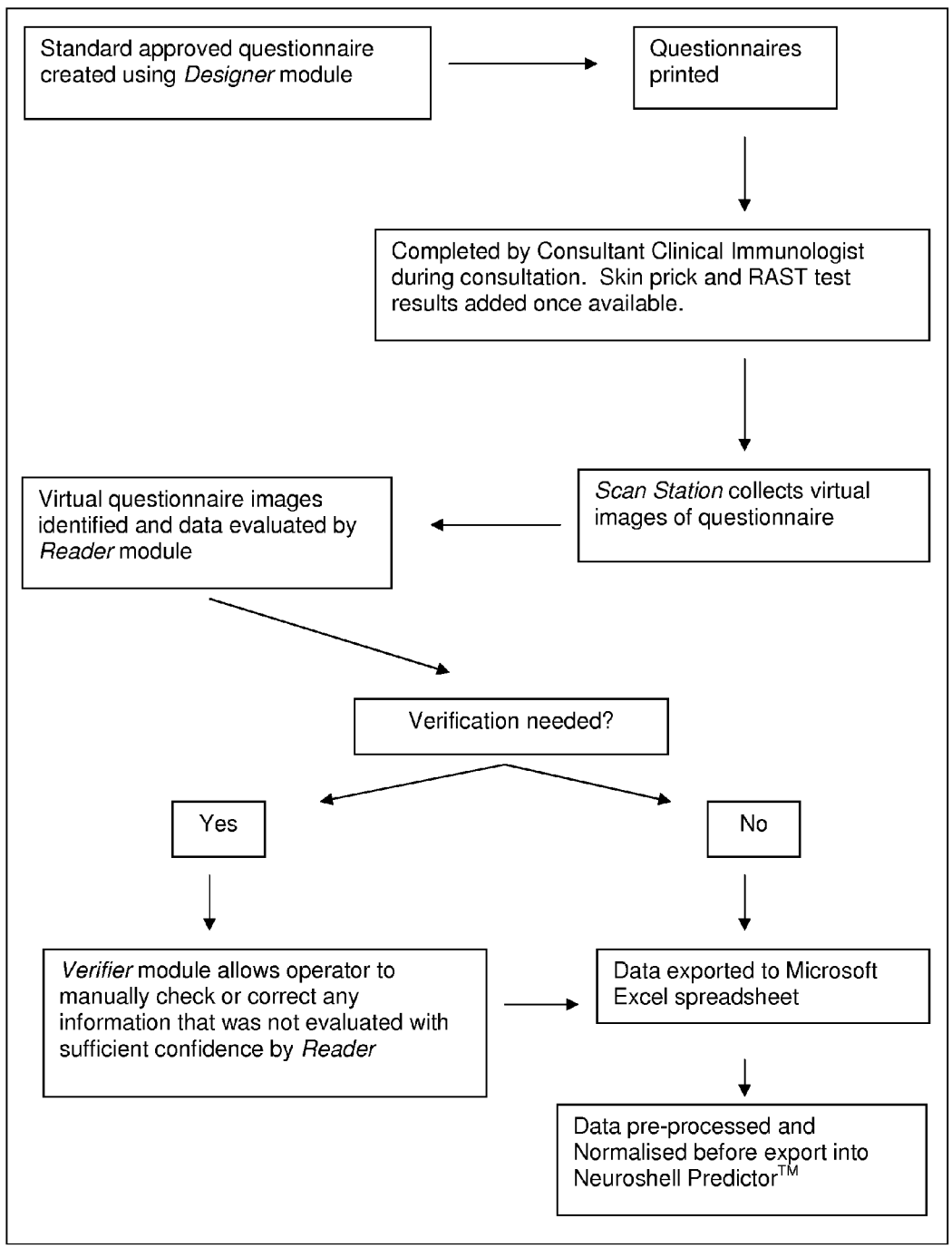
FIG. 1 is a schematic diagram of the Cardiff TELEform Information Capture System.

Table 1 shows the distribution of diagnoses in patients presenting to the Welsh Clinical Allergy Service (WCAS) outpatient clinics in 2001, and is representative of the caseload seen in this regional allergy centre. It will be seen that a high proportion of patients presented to the service with symptoms of urticaria and angioedema.

Table 1

| Distribution of diagnoses in patients seen in WCAS outpatient clinics in 2001 (n = 213) | | |
|---|---|---|
| Diagnostic Category | No. of patients with diagnosis | Percentage of all patients % |
| Urticaria/Angioedema | 46 | 21.6 |
| Rhinitis | 43 | 20.2 |
| Drug-induced angioedema/reaction | 28 | 13.1 |
| Food allergy | 26 | 12.2 |
| Food intolerance | 14 | 6.6 |
| Salicylate intolerance | 11 | 5.2 |
| Venom insensitivity | 7 | 3.3 |
| Non-allergic/miscellaneous conditions | 38 | 17.8 |
| Total | 213 | 100 |

Methods

Ethical Considerations

Bro Taf Local Research Ethics Committee granted ethical approval for all aspects of this study and the project was registered with Cardiff and Vale NHS Trust Research and Development Office. All participants were required to complete a consent form. Data were anonymised prior to analysis and handled in accordance with the Data Protection Act 1998.

Structured Questionnaire Design

This study made use of a standard questionnaire comprising questions and tests were created using the commercial Cardiff TELEform information capture system v7.0 Designer module. This questionnaire was devised as an integral part of the Nurse Practitioner-based diagnosis and management evaluation program and aimed to gather demographic and clinical information in a structured format. This questionnaire was endorsed by a multidisciplinary panel of experts and piloted in WCAS clinics throughout 2001.

Patient Recruitment and Data Collection

Data were gathered during 2004. Patients aged 18 to 75 referred to the WCAS by General Practitioners or hospital doctors due to symptoms of urticaria or angioedema were drawn from the routine non-urgent outpatient waiting list and recruited using an approved protocol. All consenting patients with predominant presenting symptoms of urticaria or angioedema were entered into the study. There were no exclusion criteria. Participants underwent Skin Prick Testing immediately prior to an initial conventional consultation with either the Consultant Clinical Immunologist or Allergy Nurse Practitioner. The order of consultation was randomized so that roughly equal numbers of patients were seen first by the Nurse Practitioner as by the Consultation Clinical Immunologist. Findings were recorded on the standard questionnaire ensuring all sections were fully completed. Patients were then seen independently by the other practitioner, and findings annotated upon a separate questionnaire. Total serum IgE and RAST testing were performed upon clinical discretion. As per current WCAS protocol, a clinic letter outlining the final diagnosis and management plan was dictated by the Consultant Clinical Immunologist and posted to the referring medical practitioner and patient. A similar letter was dictated independently by the Allergy Nurse Practitioner, which was retained as supporting evidence to her questionnaire, for analysis in a later study.

Data Transfer

Once available, all RAST and other test results were added to data recorded during respective consultations. Completed questionnaires were processed using the commercial Cardiff TELEform information capture system v8.2 Scan station, Reader and Verifier modules (see FIG. 1). Data were exported into separate Microsoft Excel files for each clinician.

Data Preprocessing and Normalisation

Data imported into Microsoft Excel were anonymised. All input variables were inspected for transfer accuracy and errors corrected manually. Data were normalised (scaled) within a uniform range for each input variable, some variables removed (e.g. domestic demographic data, ethnic origin and marital status) and a number of new input variables created following recoding of defined input groups. The final aetiological diagnosis for each patient was coded into one of five output categories (chronic idiopathic urticaria/angioedema, physical urticaria, aspiring-included urticaria, non-aspirin drug induced urticaria/angioedema, and urticaria after unidentified food additives).

Data Partitioning

Data were partitioned into two separate Excel parent databases (i.e. separate Excel worksheets) (i) 'all questionnaire inputs' and (ii) 'clinically selected inputs' (79 input variables; five output variables) (see Table 2), as it became available. ANN models were developed using data and diagnoses from the Consultant Clinical Immunologist. Model development required data from each parent database to be divided into two subsets: (i) training and test data and (ii) validation.

TABLE 2

Questions and test results utilised in 79-, 54-, 35-, 25-, 21-, 17-, 15-, 14- and 9-input models
Inputs used in different analyses

| | No of inputs used: | | | | | | | | |
|---|---|---|---|---|---|---|---|---|---|
| | 79 | 54 | 35 | 25 | 21 | 17 | 15 | 14 | 9 |
| Taking ACE inhibitor    Yes = 1    No = 0 | ✓ | ✓ | | | | | | | |
| Taking A2R antagonist | ✓ | ✓ | | | | | | | |
| Taking Statin | ✓ | ✓ | | | | | | | |
| Taking PPI | ✓ | ✓ | | | | | | | |
| Taking SSRI | ✓ | ✓ | | | | | | | |
| Taking SNRI | ✓ | ✓ | | | | | | | |
| Taking NSAID or Aspirin | ✓ | ✓ | ✓ | ✓ | ✓ | ✓ | ✓ | ✓ | ✓ |
| Taking OCPIII | ✓ | ✓ | | | | | | | |
| Taking HRT | ✓ | ✓ | | | | | | | |
| Taking Bisphosphonates | ✓ | ✓ | | | | | | | |
| Given other drugs associated with angioedema and urticaria (opiates, nicorandil, amlodipine, contrast media, chlorthalidone) | ✓ | ✓ | ✓ | ✓ | ✓ | ✓ | ✓ | ✓ | ✓ |
| Taking any drugs that can cause those symptoms complained of (urticaria, angioedema etc., abdominal symptoms etc . . . ) | ✓ | ✓ | ✓ | ✓ | ✓ | ✓ | ✓ | ✓ | ✓ |
| Tingling of the mouth/lips, swelling of the tongue, inside mouth, throat or difficulty swallowing or breathing after other medications than those known to cause urticaria or angioedema? | ✓ | ✓ | ✓ | ✓ | ✓ | ✓ | ✓ | ✓ | ✓ |
| No of pack-years smoked | ✓ | ✓ | | | | | | | |
| No of first degree relatives with asthma, rhintis, eczema | ✓ | ✓ | ✓ | ✓ | | | | | |
| Tingling of the mouth/lips, swelling of the tongue, inside mouth, throat or difficulty swallowing or breathing after foods | ✓ | ✓ | ✓ | ✓ | ✓ | ✓ | ✓ | ✓ | ✓ |
| Nausea, vomiting, abdominal pain or diarrhea after foods | ✓ | ✓ | | | | | | | |
| Nettle rash after foods | ✓ | ✓ | ✓ | | | | | | |
| Wheeze, worsening of asthma or eczema after eating foods | ✓ | ✓ | ✓ | ✓ | ✓ | ✓ | ✓ | ✓ | ✓ |
| Headaches after foods | ✓ | ✓ | | | | | | | |
| Symptoms triggered by wheat | ✓ | ✓ | ✓ | ✓ | | | | | |
| Symptoms triggered by egg | ✓ | | | | | | | | |
| Symptoms triggered by milk | ✓ | | | | | | | | |
| Symptoms triggered by cheese | ✓ | ✓ | ✓ | | | | | | |

TABLE 2-continued

Questions and test results utilised in 79-, 54-, 35-, 25-, 21-, 17-, 15-, 14- and 9-input models
Inputs used in different analyses

| | No of inputs used: | | | | | | | | |
|---|---|---|---|---|---|---|---|---|---|
| | 79 | 54 | 35 | 25 | 21 | 17 | 15 | 14 | 9 |
| Symptoms triggered by peanut | ✓ | | | | | | | | |
| Symptoms triggered by other nuts | ✓ | | | | | | | | |
| Symptoms triggered by fish | ✓ | | | | | | | | |
| Symptoms triggered by shellfish | ✓ | | | | | | | | |
| Symptoms triggered by other foods | ✓ | ✓ | ✓ | ✓ | | | | | |
| Symptoms triggered by fruit & vegetables | ✓ | ✓ | ✓ | ✓ | ✓ | ✓ | ✓ | ✓ | ✓ |
| Symptoms triggered by unidentified food additives | ✓ | ✓ | ✓ | ✓ | ✓ | ✓ | ✓ | ✓ | ✓ |
| Symptoms triggered by Aspirin, aspirin-containing drugs, orange juice, curry or high-aspirin content food | ✓ | ✓ | ✓ | ✓ | ✓ | ✓ | ✓ | ✓ | |
| No of hrs after eating these foods symptoms start | ✓ | ✓ | ✓ | ✓ | ✓ | ✓ | ✓ | ✓ | ✓ |
| How frequently these symptoms occur; Daily = 5, 2-3 times/week = 4, Weekly = 3, Monthly = 2, Less often = 1, Not present = 0 | ✓ | ✓ | ✓ | ✓ | ✓ | ✓ | ✓ | ✓ | ✓ |
| Swelling of the lips, eyelids or tongue | ✓ | ✓ | ✓ | ✓ | ✓ | | | | |
| Itchy, red, raised, burning, hot, nettle rash | ✓ | ✓ | ✓ | ✓ | ✓ | | | | |
| Area affected by the rash; face, mouth neck, limbs body, all over - continuous area = 1; 2 areas = 2; >3 areas = 3 | ✓ | ✓ | ✓ | ✓ | ✓ | ✓ | ✓ | ✓ | ✓ |
| Do new patches appear when old ones are disappearing? Yes = 2, No = 1 | ✓ | ✓ | ✓ | ✓ | ✓ | ✓ | | | |
| Do patches last more than 24 hr (2) or less than 24 hr (1) | ✓ | ✓ | | | | | | | |
| Does urticaria come on with physical stimuli of cold, wet, wind, pressure . . . | ✓ | ✓ | ✓ | ✓ | ✓ | ✓ | ✓ | ✓ | |
| How many years rash or swelling experienced | ✓ | ✓ | ✓ | ✓ | | | | | |
| If antihistamines tried for urticaria were they effective? 0 = not tried 1 = ineffective 2 = effective | ✓ | ✓ | ✓ | | | | | | |
| Graded SPT 0 = neg, 1 =< hist 2 =± hist HDM | ✓ | ✓ | ✓ | | | | | | |
| Graded SPT 0 = neg, 1 =< hist 2 =± hist Cat | ✓ | ✓ | ✓ | ✓ | ✓ | ✓ | ✓ | | |
| Graded SPT 0 = neg, 1 =< hist 2 =± hist Dog | ✓ | | | | | | | | |
| Graded SPT 0 = neg, 1 =< hist 2 =± hist Grass Pollens | ✓ | ✓ | ✓ | | | | | | |
| Graded SPT 0 = neg, 1 =< hist 2 =± hist Tree Pollens | ✓ | | | | | | | | |
| Graded SPT 0 = neg, 1 =< hist 2 =± hist Egg | ✓ | ✓ | ✓ | | | | | | |
| Graded SPT 0 = neg, 1 =< hist 2 =± hist Milk | ✓ | ✓ | ✓ | | | | | | |
| Graded SPT 0 = neg, 1 =< hist 2 =± hist Rice | ✓ | | | | | | | | |
| Graded SPT 0 = neg, 1 =< hist 2 =± hist Peanut | ✓ | | | | | | | | |
| Graded SPT 0 = neg, 1 =< hist 2 =± hist Hazelnut | ✓ | | | | | | | | |
| Graded SPT 0 = neg, 1 =< hist 2 =± hist Brazil nut | ✓ | | | | | | | | |
| Graded SPT 0 = neg, 1 =< hist 2 =± hist Almond | ✓ | | | | | | | | |
| Graded SPT 0 = neg, 1 =< hist 2 =± hist Walnut | ✓ | | | | | | | | |
| Graded SPT 0 = neg, 1 =< hist 2 =± hist to ANY nut | ✓ | ✓ | ✓ | ✓ | ✓ | ✓ | ✓ | | |
| Graded SPT 0 = neg, 1 =< hist 2 =± hist Latex | ✓ | | | | | | | | |
| Total serum [IgE] in kU/l | ✓ | ✓ | ✓ | | | | | | |
| Grade of RAST test to HDM | ✓ | ✓ | ✓ | ✓ | ✓ | | | | |
| Grade of RAST test to Cat | ✓ | ✓ | ✓ | ✓ | ✓ | ✓ | ✓ | ✓ | |
| Grade of RAST test to Dog | ✓ | | | | | | | | |
| Grade of RAST test to Grass Pollens | ✓ | ✓ | | | | | | | |
| Grade of RAST test to Tree pollens | ✓ | ✓ | ✓ | | | | | | |
| Grade of RAST test to Egg | ✓ | ✓ | | | | | | | |
| Grade of RAST test to Milk | ✓ | ✓ | ✓ | | | | | | |
| Grade of RAST test to Soya | ✓ | | | | | | | | |
| Grade of RAST test to Wheat | ✓ | ✓ | | | | | | | |
| Grade of RAST test to Fish (cod) | ✓ | | | | | | | | |
| Grade of RAST test to Rice | ✓ | | | | | | | | |
| Grade of RAST test to Peanut | ✓ | | | | | | | | |
| Grade of RAST test to Hazelnut | ✓ | | | | | | | | |
| Grade of RAST test to Brazil nut | ✓ | | | | | | | | |
| Grade of RAST test to Almond | ✓ | | | | | | | | |
| Grade of RAST test to Walnut | ✓ | | | | | | | | |
| Highest grade of RAST test to ANY nut | ✓ | ✓ | ✓ | ✓ | ✓ | | | | |
| Grade of RAST test to Latex | ✓ | | | | | | | | |
| Grade of RAST test to Apple | ✓ | ✓ | | | | | | | |
| Grade of RAST test to some other fruit, vegetable or other food (not specified in other columns) that is associated with symptoms | ✓ | ✓ | | | | | | | |
| Which other fruit, vegetable or food RAST test positive to | ✓ | ✓ | | | | | | | |

At present there are no mathematical rules governing the required size of data subsets and most ANN-based studies utilize anecdotal rules derived from experience and analogy with statistical regression techniques (Basheer and Hajmeer et al 2000). Table 3 shows the allocation of the total (108 patients) data set into training and test data subsets. Data utilised for the ANN training subset for both parent databases were drawn from patients 001-073 since these were collected first, and data from patients 074-108 were used as test data.

TABLE 3

Distribution of diagnoses for total patient dataset, training data subset and test data subset

|  | Total | Training | Test |
|---|---|---|---|
| 1 = Chronic idiopathic urticaria/angioedema | 45 | 31 | 14 |
| 2 = Physical urticaria | 12 | 8 | 4 |
| 3 = Aspirin-induced urticaria | 12 | 8 | 4 |
| 4 = Non-aspirin Drug-induced urticaria/angioedema | 27 | 18 | 9 |
| 5 = Urticaria after unidentified food additives | 12 | 8 | 4 |
|  | 108 | 73 | 35 |

Balancing of Training and Test Subset Data

It is desirable that data used in ANN training is nearly evenly distributed between output categories to prevent the ANN model generated from being biased to over-represented output classes (Swingler 1996). Table 3 shows the distribution of diagnoses amongst patients 001-074. Traditional approaches to dealing with such unbalanced data include removing examples from over-represented output classes or adding examples pertaining to under-represented classes (Basheer and Hajmeer 2000). The relatively small size of the training and test data subsets made the first option undesirable. Furthermore, whilst there is no published epidemiological data with which to compare the distribution of diagnoses in the training data subset, it seemed unlikely that significant numbers of under-represented diagnoses would be made. It was therefore decided to use unbalanced training and test data on the premise that models created would reflect what appeared to be a real-world bias to allergic and allergic angioedema in patients presenting to the WCAS.

Optimisation of ANN Architecture

The study used a commercially available ANN, the Neuroshell Predictor™ (Ward Systems Inc, Frederick, Md., USA). Neuroshell Predictor™ can operate in one of two modes. In the neural mode of analysis, the neural net that dynamically grows hidden neurons to build a model which generalises well and trains quickly. A variation of the Cascade Correlation algorithm is utilised. When applying the trained network to new data, the Neural Training Strategy may enable better results to be obtained on "noisy data" that is somewhat dissimilar from the data used to train the network.

Alternatively, the Neuroshell Predictor™ can be used in a genetic mode of analysis. A genetic algorithm is utilised, which is a variant of the General regression neural network (GRNN). The genetic training strategy trains slowly. When applying the trained network to new data, the genetic training strategy gets better results when the new data is similar to the training data. It also works better when the training data is sparse.

Neuroshell Predictor™ Data Output Format in Neural Analysis Mode

The Neuroshell Predictor™ was trained using the 79-input model in neural analysis mode using the 73 patient training data subset. Subsequently, when the trained ANN operating in this mode was presented with the test data subset from patients 74-108, the results shown in Table 4 were obtained.

TABLE 4

Results obtained with ANN trained in neural analysis mode, 79-input model

|  | Actual "Aspirin" | Actual "Food additives" | Actual "Idiopathic" | Actual "Non-aspirin drug" | Actual "Physical" | Total | Positive Predictive Value |
|---|---|---|---|---|---|---|---|
| Classified as "Aspirin" | 4 | 0 | 0 | 2 | 0 | 6 | 66.67% |
| Classified as "Food additives" | 0 | 3 | 0 | 0 | 0 | 3 | 100.00% |
| Classified as "Idiopathic" | 0 | 0 | 13 | 5 | 0 | 18 | 72.22% |
| Classified as "Non-aspirin drug" | 0 | 1 | 1 | 2 | 0 | 4 | 50.00% |
| Classified as "Physical" | 0 | 0 | 0 | 0 | 4 | 4 | 100.00% |
| Total | 4 | 4 | 14 | 9 | 4 | 35 |  |
| True-pos. ratio | 1 | 0.75 | 0.9286 | 0.2222 | 1 |  |  |
| False-pos. ratio | 0.0645 | 0 | 0.2381 | 0.0769 | 0 |  |  |
| True-neg. ratio | 0.9355 | 1 | 0.7619 | 0.9231 | 1 |  |  |
| False-neg. ratio | 0 | 0.25 | 0.0714 | 0.7778 | 0 |  |  |
| Sensitivity | 100.00% | 75.00% | 92.86% | 22.22% | 100.00% |  |  |
| Specificity | 93.55% | 100.00% | 76.19% | 92.31% | 100.00% |  |  |

Figure 2:
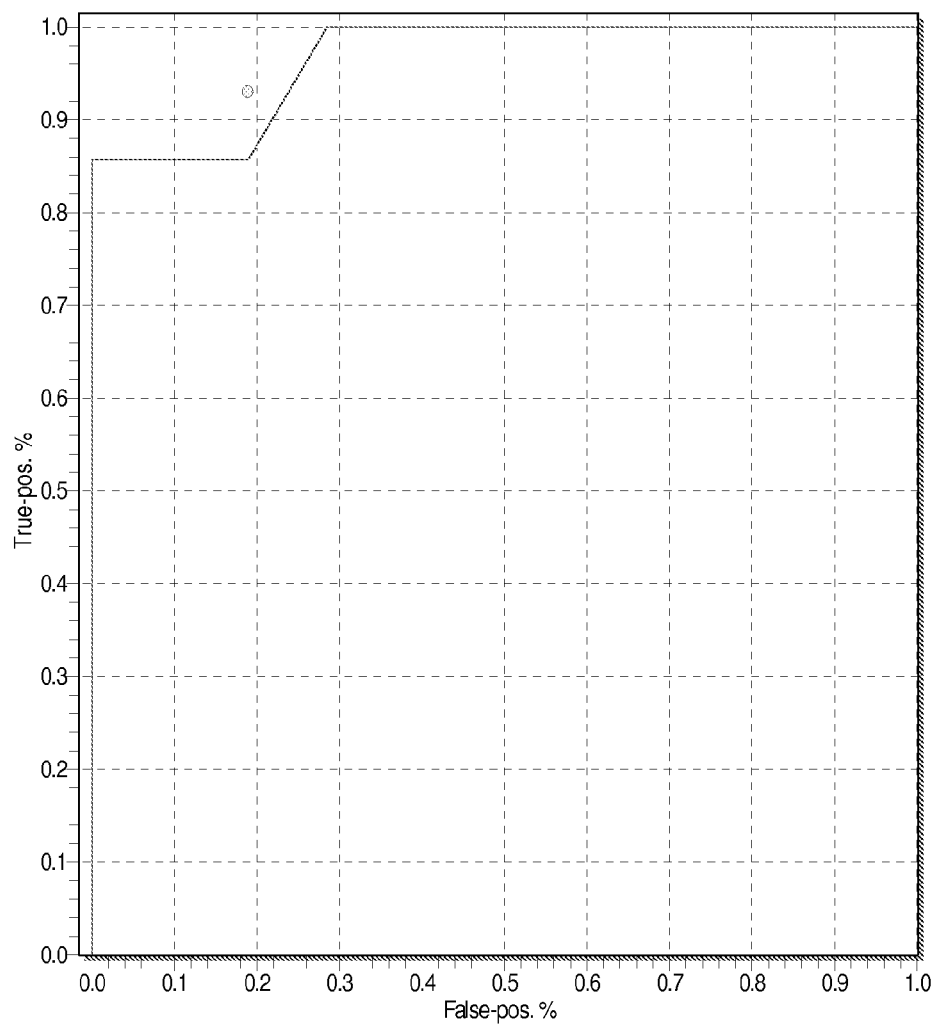
FIG. 2 is a ROC curve for the diagnosis of idiopathic urticaria with an ANN trained in neural analysis mode, 79-input model.

The associated Receiver Operating Characteristic (ROC) curve for the most common category, idiopathic urticaria, is shown in FIG. 2.

Neuroshell Predictor™ Data Output Format in Genetic Analysis Mode

The Neuroshell Predictor™ program was trained in the genetic mode of analysis using the 73 patient training data subset and the 79-input model. Subsequently, when the trained ANN was presented with the test data subset from patients 74-108, the results shown in Table 5 were obtained.

TABLE 5

Results obtained with ANN trained in genetic analysis mode, 79-input model

|  | Actual "Aspirin" | Actual "Food additives" | Actual "Idiopathic" | Actual "Non-aspirin drug" | Actual "Physical" | Total | Positive Predictive Value |
|---|---|---|---|---|---|---|---|
| Classified as "Aspirin" | 4 | 0 | 1 | 0 | 0 | 5 | 80.00% |
| Classified as "Food additives" | 0 | 2 | 0 | 0 | 0 | 2 | 100.00% |
| Classified as "Idiopathic" | 0 | 1 | 13 | 2 | 0 | 16 | 81.25% |
| Classified as "Non-aspirin drug" | 0 | 0 | 0 | 7 | 0 | 7 | 100.00% |
| Classified as "Physical" | 0 | 0 | 0 | 0 | 4 | 4 | 100.00% |
| Total | 4 | 3 | 14 | 9 | 4 | 34 |  |
| True-pos. ratio | 1 | 0.6667 | 0.9286 | 0.7778 | 1 |  |  |
| False-pos. ratio | 0.0333 | 0 | 0.15 | 0 | 0 |  |  |
| True-neg. ratio | 0.9667 | 1 | 0.85 | 1 | 1 |  |  |
| False-neg. ratio | 0 | 0.3333 | 0.0714 | 0.2222 | 0 |  |  |
| Sensitivity | 100.00% | 66.67% | 92.86% | 77.78% | 100.00% |  |  |
| Specificity | 96.67% | 100.00% | 85.00% | 100.00% | 100.00% |  |  |

Figure 3:
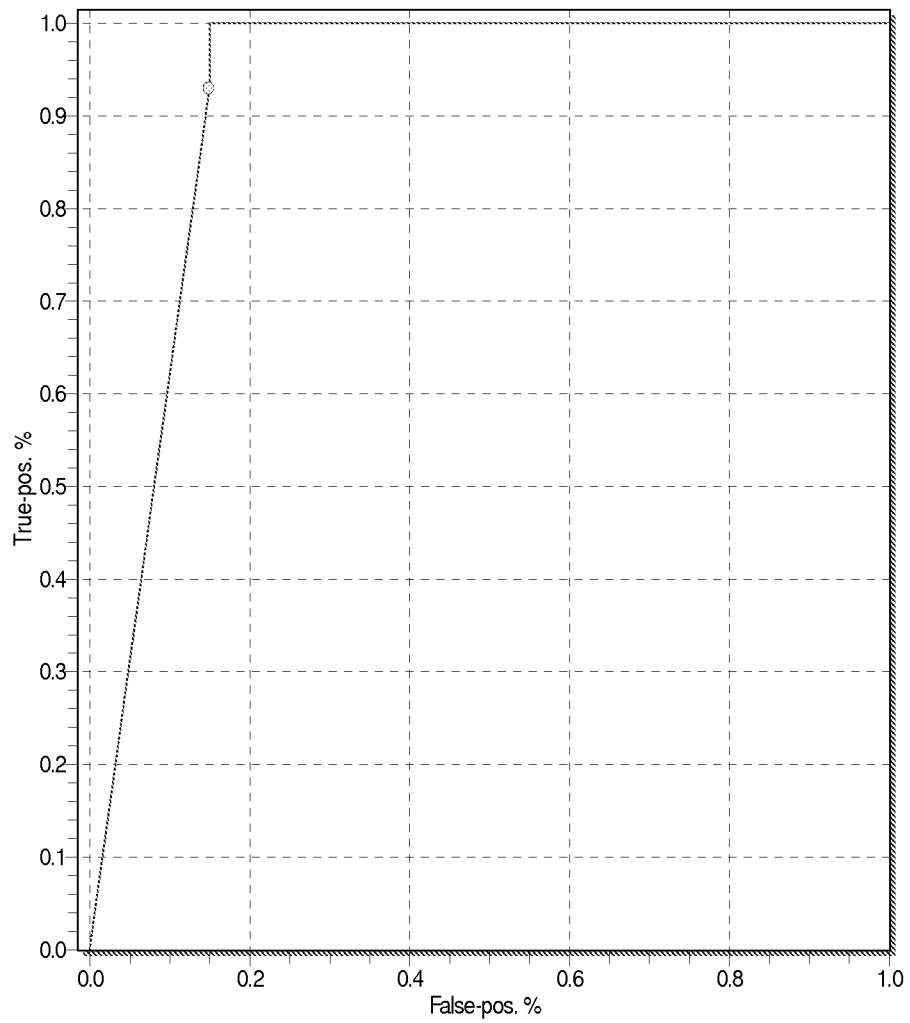
FIG. 3 is a ROC curve for the diagnosis of idiopathic urticaria with an ANN trained in genetic analysis mode, 79-input model.

The associated ROC curve for the diagnosis of idiopathic urticaria data is shown in FIG. 3. Table 6 shows the relative importance of the 79-input fields into the ANN after training using the genetic mode of analysis.

TABLE 6

Relative importance of 79 inputs in Genetic analysis mode

| INPUT | |
|---|---|
| 0.051 | tingling or swelling or difficulty swallowing or breathing after drugs |
| 0.046 | No of hrs before symptoms start after food |
| 0.040 | any other drugs that can cause symptoms complained of |
| 0.037 | Rast grade to to ANY nut |
| 0.036 | Rast grade to Cat |
| 0.036 | symptoms after aspirin or high aspirin food |
| 0.036 | ACE |
| 0.032 | SPT to Almond |
| 0.032 | symptoms after food additives |
| 0.031 | Past grade to Dog |
| 0.030 | OC Pill |
| 0.029 | How often symptoms occur with 5 daily and 0 no |
| 0.028 | PPI |
| 0.028 | no first degree relatives with asthma etc |
| 0.027 | urticaria after physical stimuli |
| 0.023 | Rast grade to HDM |
| 0.021 | NSAID or Aspirin |
| 0.021 | SPT to ANY nut |
| 0.020 | SPT to peanut |
| 0.020 | Rast grade to Grass pollens |
| 0.020 | SPT to hazelnut |
| 0.020 | new patches appear as old ones disappear |
| 0.019 | how many years swellingor rash experienced |
| 0.018 | other drugs assoc with urticana and angioedema |
| 0.018 | Rast grade to Tree pollens |
| 0.018 | symptoms after wheat |
| 0.017 | SPT to HDM |
| 0.015 | Rast grade to rice |
| 0.015 | SPT to egg |
| 0.014 | wheeze or asthma after food |
| 0.014 | Rast grade to Peanut |
| 0.014 | SPT to dog |
| 0.012 | nausea or GI syptoms after foods |
| 0.012 | STATIN |
| 0.011 | Rast grade to Egg |
| 0.010 | HRT |
| 0.009 | areas affected with 1 one area and 3 all over |
| 0.009 | symptoms after milk |
| 0.009 | symptoms after other food |
| 0.008 | nettle rash after food |
| 0.008 | symptoms after fruit and vegetables |
| 0.008 | SPT to milk |
| 0.008 | pack years smoked |
| 0.007 | SPT to Walnut |
| 0.007 | SPT to cat |

TABLE 6-continued

Relative importance of 79 inputs in Genetic analysis mode

| INPUT | |
|---|---|
| 0.007 | A2R |
| 0.006 | SPT to Brazil nut |
| 0.006 | antihistamines effective or not |
| 0.006 | patches for more or less than 24 hr |
| 0.006 | SPT to rice |
| 0.004 | Bisphosphonates |
| 0.004 | SPT to tree pollen |
| 0.004 | Rast grade to Wheat |
| 0.003 | headache after food |
| 0.003 | Rast grade to Milk |
| 0.002 | Total serum IgE |
| 0.001 | tingling or swelling etc after food |
| 0.001 | symptoms after cheese |
| 0.001 | SSRI |
| 0.000 | SPT to grass pollen |

Data Analysis with View to Optimising Data Input and Diagnosis

The information shown in Tables 4 and 5, and FIGS. 2 and 3 demonstrates that the commercially available product Neuroshell Predictor™ can be used to produce an ANN that is capable of performing a clinical diagnosis. However, further data analysis is needed in order to determine the optimum number of reliable data inputs needed to obtain an acceptable tool for diagnosis. Accordingly, the number and combination of data inputs was progressively reduced and varied, respectively, with a view to determining a preferred number and nature of inputs for producing a reliable diagnosis. This process partly involved an analysis of the relative importance of inputs into the ANN, and also utilised clinical experience and judgement. Table 2 shows, in addition to the 79-input model, 54-, 35-, 25-, 21-, 17-, 15-, 14- and 9-input models obtained by using 54, 35, 25, 21, 17, 15, 14 and 9 data inputs, respectively. Using each input model, and each mode of operation of the ANN, data was obtained concerning the ANN reliability of diagnosis vis a vis use of clinical analysis.

TABLE 7

Sensitivity and Specificity of ANN analysis on Test Data Subset as a Function of the Number of Inputs

| No of inputs | Neural Sensitivity | Neural Specificity | Genetic: minimising Av % incorrect classifications | | Genetic: minimising no of incorrect classifications | |
|---|---|---|---|---|---|---|
| | | | Sensitivity | Specificity | Sensitivity | Specificity |
| 79 | 78.02% | 92.41% | 87.46% | 96.33% | | |
| 54 | 83.89% | 94.77% | 97.78% | 99.00% | | |
| 35 | 91.35% | 97.45% | 100.00% | 100.00% | | |
| 21 | 95.00% | 99.05% | 93.57% | 98.58% | | |
| 17 | 95.00% | 99.05% | 93.57% | 98.58% | 98.57% | 99.35% |
| 15 | 100.00% | 100.00% | 95.00% | 99.23% | 95.00% | 99.23% |
| 14 | 100.00% | 100.00% | 95.00% | 99.23% | 95.00% | 99.23% |
| 9 | 46.67% | 86.97% | 50.16% | 87.22% | 44.44% | 86.33% |

TABLE 8

Sensitivities and Specificities for 14-Input Model, Neural Model

| | Actual "Aspirin" | Actual "Food Additives" | Actual "Idiopathic" | Actual "Non-aspirin Drug" | Actual "Physical" | Total | Positive Predictive Value |
|---|---|---|---|---|---|---|---|
| Classified as "Aspirin" | 4 | 0 | 0 | 0 | 0 | 4 | 100.00% |
| Classified as "Food additives" | 0 | 4 | 0 | 0 | 0 | 4 | 100.00% |
| Classified as "Idiopathic" | 0 | 0 | 14 | 0 | 0 | 14 | 100.00% |
| Classified As "Non-aspirin drug" | 0 | 0 | 0 | 9 | 0 | 9 | 100.00% |
| Classified As "Physical" | 0 | 0 | 0 | 0 | 4 | 4 | 100.00% |
| Total | 4 | 4 | 14 | 9 | 4 | 35 | |
| True-pos. ratio | 1 | 1 | 1 | 1 | 1 | | |
| False-pos. ratio | 0 | 0 | 0 | 0 | 0 | | |
| True-neg. ratio | 1 | 1 | 1 | 1 | 1 | | |
| False-neg. ratio | 0 | 0 | 0 | 0 | 0 | | |
| Sensitivity | 100.00% | 100.00% | 100.00% | 100.00% | 100.00% | | |
| Specificity | 100.00% | 100.00% | 100.00% | 100.00% | 100.00% | | |
| Mean Sensitivity | 100.00% | | | | | | |
| Mean Specificity | 100.00% | | ROC curve | for Idiopathic | urticaria Area = | | 1.0000 |

TABLE 9

Sensitivities and Specificities for 14-Input Model, Genetic Mode Minimising Average Percentage of Incorrect Classifications

| | Actual "Aspirin" | Actual "Food Additives" | Actual "Idiopathic" | Actual "Non-aspirin Drug" | Actual "Physical" | Total | Positive Predictive Value |
|---|---|---|---|---|---|---|---|
| Classified as "Aspirin" | 4 | 0 | 0 | 0 | 0 | 4 | 100.00% |
| Classified as "Food additives" | 0 | 3 | 0 | 0 | 0 | 3 | 100.00% |

TABLE 9-continued

Sensitivities and Specificities for 14-Input Model, Genetic Mode Minimising Average Percentage of Incorrect Classifications

| | Actual "Aspirin" | Actual "Food Additives" | Actual "Idiopathic" | Actual "Non-aspirin Drug" | Actual "Physical" | Total | Positive Predictive Value |
|---|---|---|---|---|---|---|---|
| Classified as "Idiopathic" | 0 | 0 | 14 | 0 | 0 | 14 | 100.00% |
| Classified As "Non-aspirin drug" | 0 | 1 | 0 | 9 | 0 | 10 | 100.00% |
| Classified As "Physical" | 0 | 0 | 0 | 0 | 4 | 4 | 100.00% |
| Total | 4 | 4 | 14 | 9 | 4 | 35 | |
| True-pos. Ratio | 1 | 0.75 | 1 | 1 | 1 | | |
| False-pos. Ratio | 0 | 0 | 0 | 0.0385 | 0 | | |
| True-neg. Ratio | 1 | 1 | 1 | 0.9615 | 1 | | |
| False-neg. Ratio | 0 | 0.25 | 0 | 0 | 0 | | |
| Sensitivity | 100.00% | 75.00% | 100.00% | 100.00% | 100.00% | | |
| Specificity | 100.00% | 100.00% | 100.00% | 96.15% | 100.00% | | |
| Mean Sensitivity | 95.00% | | | | | | |
| Mean Specificity | 99.23% | | ROC curve | for Idiopathic | urticaria Area = | | 1.0000 |

TABLE 10

Sensitivities and Specificities for 14-Input Model, Genetic Mode Minimising Total Number of Incorrect Classifications

| | Actual "Aspirin" | Actual "Food Additives" | Actual "Idiopathic" | Actual "Non-aspirin Drug" | Actual "Physical" | Total | Positive Predictive Value |
|---|---|---|---|---|---|---|---|
| Classified as "Aspirin" | 4 | 0 | 0 | 0 | 0 | 4 | 100.00% |
| Classified as "Food additives" | 0 | 3 | 0 | 0 | 0 | 3 | 100.00% |
| Classified as "Idiopathic" | 0 | 0 | 14 | 0 | 0 | 14 | 100.00% |
| Classified As "Non-aspirin drug" | 0 | 1 | 0 | 9 | 0 | 10 | 90.00% |
| Classified As "Physical" | 0 | 0 | 0 | 0 | 4 | 4 | 100.00% |
| Total | 4 | 4 | 14 | 9 | 4 | 35 | |
| True-pos. Ratio | 1 | 0.75 | 1 | 1 | 1 | | |
| False-pos. Ratio | 0 | 0 | 0 | 0.0385 | 0 | | |
| True-neg. Ratio | 1 | 1 | 1 | 0.9615 | 1 | | |
| False-neg. Ratio | 0 | 0.25 | 0 | 0 | 0 | | |
| Sensitivity | 100.00% | 75.00% | 100.00% | 100.00% | 100.00% | | |
| Specificity | 100.00% | 100.00% | 100.00% | 96.15% | 100.00% | | |
| Mean Sensitivity | 95.00% | | | | | | |
| Mean Specificity | 99.23% | | ROC curve | for Idiopathic | urticaria Area = | | 1.0000 |

Table 7 shows the mean sensitivities and specificities across all five output diagnostic categories as a function of the number of input fields utilised. The results are shown separately for the ANN trained in the neural mode of analysis, in the genetic mode of analysis when trained to minimise the average number of incorrect classifications over all categories and in the genetic mode of analysis when trained to minimise the total number of incorrect classifications. Tables 8-10 show sensitivities and specificities across the five output diagnostic categories for the 14-input model for the differently trained ANNs. It can be seen that the reduced inputs set of 14 to 54 inputs provide good or excellent categorisation of urticaria/angioedema by aetiological cause. The 14 inputs were reduced to 9 inputs by eliminating the following 5 inputs from the analysis:

1. Taking NSAID or Aspirin
2. Symptoms triggered by Aspirin, aspirin-containing drugs, orange juice, curry or high-aspirin content food
3. The presence and amount of IgE antibodies against Cat in a RAST test
4. Tingling of the mouth/lips, swelling of the tongue, inside mouth, throat or difficulty swallowing or breathing after other medications than those known to cause urticaria or angioedema
5. Urticaria coming on with physical stimuli of cold, wet, wind, pressure etc.

However, it was found that the removal of these 5 inputs resulted in a marked degradation of the ANN's performance, with sensitivities falling to 50% or below. From this it was inferred that a meaningful classification of urticaria/angioedema by aetiological cause should utilise an input data set which includes these five inputs. Of course, other inputs may be included as well. The removal of other combinations of 5 inputs from the 14-input model did not result in such a marked degradation in ANN performance.

Other forms of neural network and trained methodologies might be employed. For example, it may be desirable to analyse the data in a series of steps. For instance, an initial, broad diagnosis might be provided, with more detailed classifications into specific aetiological causes being provided in one or more further steps. A different and/or differently trained neural network may be used for a subsequent step, and a different subset of questions and/or test results might be used in order to make the more refined diagnosis.

REFERENCES

Basheer, I, A and Hajmeer, M. (2000). 'Artificial neural networks: fundamentals, computing, design and application'. *J. Microbiol Methods* 43: 3-31.
Baxt, W, G. (1995). 'Application of Artificial Neural Networks to Clinical Medicine.' *Lancet* 346: 1135-1138.
Callan, R. (1999). '*The Essence of Neural Networks*'. Hemel Hempstead: Prentice Hall Europe.
Das, A; Ben-Menachem, T; Cooper, G, S, et al. (2003). 'Prediction of outcome in acute lower-gastrointestinal haemorrhage based on an artificial neural network: internal and external validation of a predictive model.' *Lancet* 362: 1261-1266.
Dybowski, R and Gant, V (eds) (2001). '*Clinical Applications of Artificial Neural Networks*'. Cambridge: Cambridge University Press.
Hanley, J, A and McNeil, B, J. (1982). 'The meaning and use of the Area under a Receiver Operating Characteristic (ROC) Curve.' *Radiology* 143: 29-36.
Hecht-Nielsen, R. (1990). '*Neurocomputing*'. Massachusetts: Addison-Wesley.
Holgate, S, T and Broide, D. (2003). 'New targets for allergic rhinitis—a disease of civilisation'. *Nature Rev Drug Discovery* 2: 1-12.
Lancashire, L, J; Mian, S; Rees, R, C, et al. (2003). 'Preliminary artificial neural network analysis of SELDI mass spectrometry data for the classification of melanoma tissue'. *Proceedings of the 17th European Stimulation Multiconference*.
Linneberg, A; Nielsen, N, H; Madsen, F, et al. (2000). 'Increasing prevalence of specific IgE to aeroallergens in an adult population: two cross-sectional surveys 8 years apart: the Copenhagen Allergy Study'. *J. Allergy and Clin Imm* 106: 247-252.
McCulloh, W, S and Pitts, W. (1943). 'A logical calculus of the ideas immanent in nervous activity.' *Bull. Math. Biophys* 5: 115-133.
Metz, C, E. (1978). 'Basic principles of ROC analysis.' *Semin. Nuc Med* 8: 283-298.
Roadknight, C; Palmer-Brown, D and Al-Dabass, D. (1997). 'Simulation of correlation activity pruning methods to enhance transparency of ANNs.' *Int. J. Simulation* 4: 68-74.
Rosenblatt, F. (1958). 'The perceptron: a probabilistic model for information storage and organisation in the brain.' *Psychol Rev* 65: 386-408.
Rumelhart, D, E and McClelland, J, L. (1986). '*Parallel distribution processing: Explorations in the microstructure of cognition: Volume 1: Foundations*'. Cambridge USA: MIT Press.
Schalkoff, R, J. (1977). '*Artificial Neural Networks*'. New York: McGraw-Hill.
Swingler, K. (1996). '*Applying Neural Networks: A Practical Guide*'. New York: Academic Press
Thompson, R. A, Bird A. G (1983). How necessary are specific IgE antibody tests in allergy diagnosis? *Lancet,* 321, 169-173.
Wei, J, T; Zhang, Z; Barnhill S, D, et al. (1998). 'Understanding artificial neural networks and exploring their potential applications for the practicing urologist'. *Urology* 52: 161-172.
Wide, L, Bennich H, Johansson S G O (1967). Diagnosis of allergy by an in vitro test for allergen antibodies. *Lancet,* 2:1105.
Zweig, M, H and Campbell, G. (1993). 'Receiver-Operating Characteristic (ROC) plots: a fundamental evaluation tool in clinical medicine.' *Clin. Chem* 39: 561-577.

The invention claimed is:
1. A method for diagnosing urticaria or angioedema including:
(a) asking a patient the following questions:
   are any NSAIDs or aspiring being taken;
   are symptoms triggered by aspirin, aspirin-containing drugs, orange juice, curry or high-aspirin content food;
   is tingling of the mouth or lips, swelling of the tongue, the inside of the mouth or throat, difficulty swallowing, or difficulty breathing experienced after other medications than those known to cause urticaria or angioedema;
   does urticaria or angioedema come on with physical stimuli such as cold, wet, wind and pressure;
(b) carrying out one or more tests which includes a RAST test to cat;
(c) inputting the results of the questions and tests into a neural network that has been trained to diagnose urticaria or angioedema; and
(d) producing an output indicative of urticaria or angioedema.

2. A method according to claim 1 in which part (a) further includes asking the patient the following questions:
- are any drugs that are associated with urticaria or angioedema, other than ACE inhibitors, A2R antagonists, statins, PPI, SSRI, SNRI, NSAIDs, aspirin, OCPiII, HRT, or biphosphates, being taken; optionally, are any other drugs which can cause the symptoms complained of being taken or have recently been taken;
- is tingling of the mouth or lips, swelling of the tongue, the inside of the mouth or throat, difficulty swallowing, or difficulty breathing experienced after foods;
- is wheezing or a worsening of asthma or eczema experienced after eating foods;
- are symptoms triggered by fruit and vegetables;
- are symptoms triggered by food additives;
- the time elapsed between eating a food implicated with causing symptoms and the symptoms appearing;
- how frequently the symptoms occur; and
- what areas of the body are affected by a rash.

3. A method according to claim 1 in which part (b) further includes carrying out a skin prick test to cat.

4. A method according to claim 1 in which: part (a) further includes asking the patient the following question:
- do new rash patches appear when old rash patches are disappearing;

and part (b) further includes carrying out a skin prick test to a plurality of nuts to determine if there is a reactivity to any one of them.

5. A method according to claim 1 in which: part (a) further includes asking the patient the following questions:
- is swelling of the lips, eyelids or tongue experienced;
- is an itchy, red, raised, burning and hot nettle rash experienced;

part (b) further includes carrying out the following tests;
- RAST test to HDM;
- RAST test to a plurality of nuts in order to determine the highest quantitative result;
- and part (c) includes inputting the highest quantitative result from the RAST test to the plurality of nuts.

6. A method according to claim 1 in which:
part (a) further includes asking the patient the following questions:
- number of first degree relatives with asthma, rhinitis or eczema;
- are symptoms triggered by wheat;
- are symptoms triggered by foods other than wheat, egg, milk, cheese, peanut, other nuts, fish or shellfish;
- length of time that rash or swelling has been experienced.

7. A method according to claim 1 in which: part (a) further includes asking the patient the following questions:
- is a nettle rash experienced after foods;
- are symptoms triggered by cheese;
- if antihistamines have been taken for urticaria, were they effective;

and part (b) further includes carrying out the following tests:
- skin prick test to HDM;
- skin prick test to grass pollens;
- skin prick test to egg;
- skin prick test to milk;
- total serum (IgE) detected;
- RAST test to tree pollens;
- RAST test to milk.

8. A method according to claim 1 in which:
part (a) further includes asking the patient the following questions:
- is an ACE inhibitor being taken;
- is an A2R antagonist being taken;
- is a statin being taken;
- is PPI being taken;
- is SSRI being taken;
- is SNRI being taken;
- is OCPiII being taken;
- is HRT being taken;
- is a bisphosphonate being taken;
- number of pack years smoked;
- is nausea, vomiting, abdominal pain or diarrhea experienced after foods;
- are headaches experienced after foods;
- how long do rash patches last for;

part (b) further includes carrying out the following tests:
- RAST test to grass pollens;
- RAST test to egg;
- RAST test to wheat;
- RAST test to apple;
- RAST test to any fruit, vegetable or other food (other than egg, milk, soya, wheat, fish, rice, peanut, hazelnut, brazil nut, almond, walnut or apple) associated with symptoms;

and part (c) includes inputting which fruit, vegetables or other food associated with the symptoms and the results of the associated RAST tests.

9. A method according to claim 1 in which: part (a) further includes asking the patient the following questions:
- are symptoms triggered by egg;
- are symptoms triggered by milk;
- are symptoms triggered by peanut;
- are symptoms triggered by other nuts;
- are symptoms triggered by fish;
- are symptoms triggered by shellfish;

and part (b) further includes carrying out the following tests:
- skin prick tests for dog, tree pollens, rice, peanut; hazelnut, brazil nut, almond, walnut, and latex;
- RAST tests for dog, soya, fish, rice, peanut, hazelnut, brazil nut, almond, walnut, and latex.

10. A method according to claim 1 in which one or more of the tests involves the provision of a quantitative result relating to the amount of allergen-specific IgE antibodies present.

11. A method according to claim 1 in which urticaria or angioedema is diagnosed according to aetiological cause.

12. A method according to claim 11 in which at least one of chronic idiopathic urticaria/angioedema, physical urticaria, aspiring-induced urticaria, non-aspirin drug-induced urticaria/angioedema, and food additive-induced urticaria can be diagnosed by the neural network.

13. A computer system or apparatus, configured to aid in the diagnosis of urticaria or angioedema, including:
- (a) a device for obtaining data relating to a patient, wherein the data include the results of the combination of questions and of tests according to claim 1;
- (b) optionally, a device for storing the data in storage means of the computer system;
- (c) a device for transferring the data to a neural network trained on samples of the data; and
- (d) a device for extracting from the trained neural network an output, the output being an indicator for the diagnosis of urticaria or angioedema.

14. A neural network to aid in the diagnosis of urticaria or angioedema, the neural network including:
- an input layer having a plurality of input nodes into which can be inputted data which include the results of a combination of questions and tests according to claim 1; and
- an output layer for producing an output;
- in which the neural network is trained on data relating to a group of patients in which urticaria or angioedema is present, wherein the data include said results of said combination of questions and tests according to claim 1, so that the neural network is configured to identify a pattern of data which corresponds to urticaria or angioedema by the output layer producing an output indicative of the diagnosis of urticaria or angioedema.

15. A method for training a neural network to aid in diagnosing urticaria or angioedema, including:
(a) obtaining data relating to a group of patients in which urticaria or angioedema known, wherein the data include a combination of the results of the questions and tests according to claim 1;
(b) training a neural network to identify a pattern of data which corresponds to urticaria or angioedema; and
(c) storing the neural network in storage means of a computer or on a computer-readable medium.

16. A computer program product including:
a computer usable medium having computer readable program code and computer readable system code embodied on said medium for aiding in the diagnosis of urticaria or angioedema, said computer program product including:
computer program code means, when the program code is loaded, to make the computer execute a procedure to:
(a) obtain data relating to a patient, wherein the data include the results of a combination of questions and tests according to claim 1;
(b) optionally, store the data; (c) transfer the data to a neural network trained on the aforementioned data; and
(d) extract from the trained neural network an output, the output being an indicator for the diagnosis of urticaria or angioedema.

17. A computer system including a first means for:
(a) obtaining data relating to a patient, wherein the data includes the results of a combination of questions and tests outlined according to claim 1; and a second remote means, wherein said second means includes means for:
(b) optionally, storing the data;
(c) transferring the data to a neural network trained on the aforementioned data; and
(d) extracting from the trained neural network on output, the output being an indicator for the diagnosis of urticaria or angioedema.

* * * * *